US008663995B2

(12) United States Patent
Sakata et al.

(10) Patent No.: US 8,663,995 B2
(45) Date of Patent: Mar. 4, 2014

(54) METHOD FOR ANALYZING AQUEOUS AMMONIUM CARBAMATE SOLUTION, AND METHOD FOR OPERATING UNREACTED GAS ABSORBER

(75) Inventors: Eiji Sakata, Narashino (JP); Kenji Yoshimoto, Narashino (JP); Shuhei Nakamura, Narashino (JP)

(73) Assignee: Toyo Engineering Corporation, Tokyo (JP)

( * ) Notice: Subject to any disclaimer, the term of this patent is extended or adjusted under 35 U.S.C. 154(b) by 9 days.

(21) Appl. No.: 13/321,529

(22) PCT Filed: May 12, 2010

(86) PCT No.: PCT/JP2010/057989
§ 371 (c)(1),
(2), (4) Date: Nov. 18, 2011

(87) PCT Pub. No.: WO2010/137454
PCT Pub. Date: Dec. 2, 2010

(65) Prior Publication Data
US 2012/0060931 A1  Mar. 15, 2012

(30) Foreign Application Priority Data

May 28, 2009 (JP) ................................. 2009-128839

(51) Int. Cl.
*F17D 3/00* (2006.01)
*G01N 33/18* (2006.01)
*G01N 33/00* (2006.01)

(52) U.S. Cl.
USPC ................ 436/113; 436/111; 137/1; 73/19.1; 73/19.01

(58) Field of Classification Search
USPC .............. 137/1; 73/19.1, 19.01; 436/111, 113
See application file for complete search history.

(56) References Cited

U.S. PATENT DOCUMENTS

| | | |
|---|---|---|
| 3,270,050 A | 8/1966 | Mavrovic |
| 3,981,684 A | 9/1976 | Mavrovic |
| 4,572,830 A | 2/1986 | Biermans et al. |
| 6,518,457 B1 | 2/2003 | Sakata et al. |
| 2002/0082451 A1 | 6/2002 | Yoshida et al. |
| 2006/0270872 A1 | 11/2006 | Kojima |
| 2009/0036712 A1 | 2/2009 | Kojima |

FOREIGN PATENT DOCUMENTS

| | | |
|---|---|---|
| CN | 101166714 A | 4/2008 |
| GB | 2110675 A | 6/1983 |
| JP | 47-10226 A | 5/1972 |
| JP | 58-90544 A | 5/1983 |
| JP | 59-133451 A | 7/1984 |
| JP | 6-184085 A | 7/1994 |
| JP | 10-182586 A | 7/1998 |
| JP | 2002-145850 A | 5/2002 |
| JP | 2003-104949 A | 4/2003 |
| JP | 2006-335653 A | 12/2006 |

OTHER PUBLICATIONS

Shen, Hua min, Progress with passing time for urea technology, Chemical Fertilizer Design, Jun. 2004, pp. 6-11, China.
Office Action issued Dec. 26, 2013 in corresponding Chinese Application No. 201080022989.6 with partial translation.

*Primary Examiner* — Christine T Mui
(74) *Attorney, Agent, or Firm* — Knobbe Martens Olson & Bear LLP

(57) ABSTRACT

There are provided a method for analyzing an aqueous ammonium carbamate solution whereby the composition of an unreacted-gas absorber outlet liquid can be specified in real time, and a method for operating an unreacted gas absorber by use of the same. The method for analyzing the composition of an aqueous ammonium carbamate solution includes determining ammonia component concentration, carbon dioxide component concentration, and water concentration of the aqueous ammonium carbamate solution, which is the unreacted-gas absorber outlet liquid in a urea production process, by using a correlation among viscosity, temperature, and carbon dioxide component concentration of the aqueous solution and a correlation among density, temperature, ammonia component concentration, and carbon dioxide component concentration of the aqueous solution, wherein the ammonia component concentration is a concentration of a sum of free ammonia and equivalent ammonia of ammonium carbamate which are contained in the aqueous solution, and the carbon dioxide component concentration is a concentration of equivalent carbon dioxide of ammonium carbamate contained in the aqueous solution.

7 Claims, 5 Drawing Sheets conc.: concentration

US 8,663,995 B2

METHOD FOR ANALYZING AQUEOUS AMMONIUM CARBAMATE SOLUTION, AND METHOD FOR OPERATING UNREACTED GAS ABSORBER

CROSS-REFERENCE TO RELATED APPLICATIONS

This application is the U.S. National Phase under 35. U.S.C. §371 of International Application PCT/JP2010/057989, filed May 12, 2010, which claims priority to Japanese Patent Application No. 2009-128839, filed May 28, 2009. The International Application was published under PCT Article 21(2) in a language other than English.

TECHNICAL FIELD

The present invention relates to an analytical method for analyzing the composition of an aqueous ammonium carbamate solution, which is an unreacted-gas absorber outlet liquid in a urea production process.

The present invention also relates to a method for operating an unreacted gas absorber in a urea production plant by use of the method for analyzing an aqueous ammonium carbamate solution.

BACKGROUND ART

In a plant for producing urea, melamine, or the like, since ammonia, carbon dioxide, water, and the like are used in the plant, an aqueous ammonium carbamate solution is present as a recycled fluid of an unreacted material, a by-product, and/or a raw material in many cases. Accordingly, for operating such a plant, it is desired that the component composition of the aqueous ammonium carbamate solution be simultaneously measured quickly without a time lag with a simple apparatus.

Hereinafter, the outline of a urea production plant will be described using FIG. 4.

As shown in FIG. 4, urea is produced through the sections of synthesis section 31, decomposition section 32, concentration section 33, and finishing section 34. In the synthesis section 31, ammonia is allowed to react with carbon dioxide to synthesize urea to provide a urea synthesis solution. Unreacted ammonia and ammonium carbamate contained in the synthesis solution are separated as a mixed gas of ammonia, carbon dioxide, and water in the decomposition section 32. To absorption section 35, is fed water (condensed water separated in the concentration section 33 may be used) as an absorbent, and the mixed gas separated in the decomposition section is absorbed into the absorbent. For this absorption, an absorber (referred to as an unreacted gas absorber) is used. An outlet liquid from the absorption section (unreacted-gas absorber outlet liquid) is returned to the synthesis section 31 as a recovered liquid.

In the production plant of urea, it is desired that the loss of ammonia and carbon dioxide to the outside of the urea production plant be eliminated by allowing all the mixed gas separated in the decomposition section to be absorbed into the absorbent and recovering it into the synthesis section as an absorbent liquid. In order to allow all the mixed gas to be absorbed into the absorbent, the plant needs to be operated so that operating temperature is always kept lower than the equilibrium temperature. On the contrary, when the operating temperature is higher than the equilibrium temperature, it is impossible to absorb the whole mixed gas. The equilibrium temperature as described herein refers to a temperature at which the liquid composition at the time when the mixed gas to be absorbed is absorbed by an absorbent (water) is exactly in a vapor-liquid equilibrium state at a controlled operating pressure. The equilibrium temperature is determined by the concentrations of ammonia, carbon dioxide, and water.

For example, if the absorbent (water) is excessively fed to the absorption section, the equilibrium temperature will increase, which is advantageous to the absorption of the mixed gas. However, on the other hand, the excessive water increases the amount of water in the outlet recovered liquid from the absorption section to thereby increase the amount of water in the urea reactor (provided in the synthesis section) which receives the recovered liquid. Therefore, the urea synthesis rate in the urea synthetic reaction is reduced to increase an unreacted material in the urea synthesis solution. This results in a vicious cycle whereby the amount of heat required to remove the unreacted material is increased to increase the steam consumption in the urea plant, and also the amount of the absorbent (water) required to recover the separated unreacted gas is further increased. Therefore, it is important for the operation that the amount of water fed to the absorber in the absorption section be the requisite minimum. However, if the amount of water fed to the absorber is carelessly reduced, the equilibrium temperature of the outlet liquid from the absorption section may be lower than the operating temperature, thereby lowering absorption performance, which may cause the loss of ammonia and carbon dioxide. At this time, the operating temperature may be decreased in order to limit the amount of water fed to the absorber and improve the absorption performance. But, if the operating temperature is excessively reduced, the operating temperature may be lower than the solidification temperature (temperature at which ammonium carbamate cannot be dissolved in the recovered liquid but is precipitated as a crystalline salt) to solidify the recovered liquid, resulting in being impossible to continue operation. The solidification temperature is also determined by the concentrations of ammonia, carbon dioxide, and water. That is, it is desirable to always keep the operating temperature in the absorption section lower than the equilibrium temperature of the recovered liquid, to make the solidification temperature of the recovered liquid be higher, and to make the difference between the equilibrium temperature and the solidification temperature be small.

The equilibrium temperature and the solidification temperature of the recovered liquid are determined by the concentrations of three components of ammonia, carbon dioxide, and water, and are not determined only by the ratio of the amount of water to carbon dioxide, or the ratio of the amount of ammonia to carbon dioxide. In order to specify the equilibrium temperature and the solidification temperature of the recovered liquid, it is required to measure the concentrations of three components accurately and simultaneously without a time lag.

By the way, as a urea synthesis process, there is known a solution circulation process in which a urea synthesis solution from a synthesis reactor in the synthesis section is directly transferred to the decomposition section. Further, there is known a stripping process in which the urea synthesis solution from the synthesis reactor is transferred to a stripper in the synthesis section, and ammonia and carbon dioxide contained in the urea synthesis solution are stripped at a synthesis pressure using carbon dioxide as a stripping agent to be removed to certain concentrations.

Particularly in the stripping process, the ammonia concentration and the carbon dioxide concentration in the outlet liquid from the stripper used vary with the operating temperature of the stripper, the feed rate of carbon dioxide, the amount of feed liquid, and the like and influence the composition of the recovered liquid. That is, since the amounts of ammonia and carbon dioxide transferred to the unreacted gas absorber easily vary with the stripping performance of the stripper, it is difficult to control the amount of water fed to the unreacted gas absorber to the optimum amount in consideration of the equilibrium temperature and the solidification temperature of the aqueous ammonium carbamate solution present in the unreacted gas absorber. Therefore, in order to continue stable operation, the feed rate of water as an absorbent is generally increased somewhat to excess.

Accordingly, if the composition of the recovered liquid is simultaneously specified without a time lag, it will be possible to accurately find the equilibrium temperature and the solidification temperature of the recovered liquid (aqueous ammonium carbamate solution) from the resulting composition, thereby making it possible to determine an optimum operating temperature and to perform the operation with controlling the amount of water in the recovered liquid to a requisite minimum amount, in consideration of both the equilibrium temperature and the solidification temperature.

Various techniques have been proposed in order to analyze the physical properties of the unreacted-gas absorber outlet liquid.

Patent Literature 1 (JP6-184085A) discloses a method of measuring the electric conductivity of an unreacted-gas absorber outlet liquid to specify carbon dioxide concentration (ammonium carbamate concentration). However, this method cannot specify the concentrations of ammonia and water in a recovered liquid, and therefore cannot exactly determine an optimal point of operation.

Patent Literature 2 (JP59-133451A) discloses a method of specifying the concentrations of ammonia and carbon dioxide by determining density and a saturation temperature by means of an oscillation-type density meter and a photometer (measurement of crystal precipitation temperature). However, in this method, a photometer is used to measure a crystal precipitation temperature, and it is necessary to adjust the temperature of an unreacted-gas absorber outlet liquid to thereby cool the solution, in order to actually precipitate crystals from a sample of the unreacted-gas absorber outlet liquid. Such a procedure causes a time lag, and therefore this method is unsuitable for operation control.

Patent Literature 3 (U.S. Pat. No. 3,270,050A) proposes a method of keeping the concentration of an unreacted-gas absorber outlet liquid at a constant level by changing the amount of water fed as an absorbent using a viscometer, in a solution circulation process which is one of urea synthesis processes. However, this method only monitors the variation of concentration by use of viscosity and is not a method of specifying the composition of the unreacted-gas absorber outlet liquid. Further, the inventor of Patent Literature 3 himself admits in Patent Literature 4 (JP47-10226A) that viscosity is unsuitable for controlling the amount of water fed as an absorbent because there is influence of free ammonia in the method according to Patent Literature 3, and proposes in Patent Literature 4 a method in which a refractometer is used instead. Thus, it is clear that the composition of the three components cannot be specified by the method described in Patent Literature 3. Also from this point, it can be said that the method described in Patent Literature 3 cannot specify the concentrations. Furthermore, also in the method described in Patent Literature 4, only the concentration of ammonium carbamate is measured by a measurement with a refractometer, and similarly to Patent Literature 3, the whole composition of the unreacted-gas absorber outlet liquid cannot be specified.

Further, although a measuring object is different from the unreacted-gas absorber outlet liquid, Patent Literature 5 (JP58-90544A) discloses a method of specifying ammonium concentration by titration, carbon dioxide concentration by electric conductivity, and urea concentration by a colorimetric method with respect to the composition of a synthesis solution in a synthesis reactor. However, they are not different from the conventional manual analysis and require time for obtaining measurement results. Therefore, the method is unsuitable for operation control. The purpose of this method is adjustment of the amount of raw-material ammonia and carbon dioxide to be fed to the synthesis reactor, and cannot be used for optimization of the absorption section.

Patent Literature 6 (JP10-182586A) and Patent Literature 7 (JP2006-335653A) disclose a method in which the N/C ratio (ammonia/carbon dioxide ratio) of an outlet liquid from a synthesis reactor or an outlet liquid from a carbamate condenser is measured by density in a synthetic system of a stripping process. The methods described in these literatures specify the ratio of ammonia to carbon dioxide, the ammonia being total ammonia including urea, carbamic acid, and unreacted ammonia in a synthesis solution, and the composition of a synthesis solution cannot be specified. Further, the purpose of these methods is adjustment of the amounts of raw-material ammonia and carbon dioxide to be fed to the synthesis reactor, and these methods cannot be used for optimization of the absorption section.

PRIOR ART LITERATURES

Patent Literature

Patent Literature 1: JP6-184085A
Patent Literature 2: JP59-133451A
Patent Literature 3: U.S. Pat. No. 3,270,050A
Patent Literature 4: JP47-1 0226A
Patent Literature 5: JP58-90544A
Patent Literature 6: JP10-182586A
Patent Literature 7: JP2006-335653A

SUMMARY OF INVENTION

Problems to be Solved by the Invention

Thus, in the conventional art, the concentrations of ammonia, carbon dioxide, and water in an aqueous ammonium carbamate solution, which is an unreacted-gas absorber outlet liquid, cannot be specified, or analysis such as crystallization or titration is required to specify these concentrations, and there has not been known any method suitable for plant control in which the composition of the aqueous ammonium carbamate solution can be specified in real time.

An object of the present invention is to provide a method for analyzing an aqueous ammonium carbamate solution whereby the composition of an unreacted-gas absorber outlet liquid can be specified in real time, and a method for operating an unreacted gas absorber by use of the same.

Means for Solving the Problems

The inventors have achieved the present invention as a result of extensive studies focusing on the fact that a typical composition of the aqueous ammonium carbamate solution which is the outlet liquid of the absorber in a urea production process includes 20 to 40 mass % of an ammonia component, 20 to 42 mass % of a carbon dioxide component, and a very small amount (0 to 2 mass %) of urea, with the balance being water; the viscosity of the aqueous solution is sensitive to the carbon dioxide component concentration in the aqueous solution and insensitive to the ammonia component concentration; the density of the aqueous solution is sensitive to the ammonia component concentration; and an oscillation-type measuring sensor can continuously measure the viscosity, density, and temperature of the aqueous solution in the state as it is (without cooling or dilution) simultaneously without a time lag. Further, the concentration of urea contained in the absorber outlet liquid is low enough, and the influence thereof on the viscosity and density is small and negligible.

Here, the "ammonia component" refers to the sum of equivalent ammonia of ammonium carbamate and free ammonia. Since one molecule of ammonium carbamate ($NH_2COONH_4$) contains two molecules of ammonia, the amount of the equivalent ammonia calculated from ammonium carbamate is 0.44 when the amount of ammonium carbamate is 1, on the mass basis. Consequently, when a liquid contains $C^1$ mass % of ammonium carbamate and $C^2$ mass % of free ammonia, the ammonia component concentration will be $(0.44 \times C^1 + C^2)$ mass %.

Further, the "carbon dioxide component" means equivalent carbon dioxide of ammonium carbamate. Therefore, when a liquid contains $C^3$ mass % of ammonium carbamate, the carbon dioxide component concentration will be $(0.56 \times C^3)$ mass %.

The present invention provides the following methods.

1) A composition analysis method for analyzing the composition of an aqueous ammonium carbamate solution, including:

determining ammonia component concentration, carbon dioxide component concentration, and water concentration of the aqueous ammonium carbamate solution, which is an unreacted-gas absorber outlet liquid in a urea production process, by using a first correlation which is a correlation among viscosity, temperature, and carbon dioxide component concentration of the aqueous solution, and a second correlation which is a correlation among density, temperature, ammonia component concentration, and carbon dioxide component concentration of the aqueous solution, wherein the ammonia component concentration is a concentration of a sum of free ammonia and equivalent ammonia of ammonium carbamate which are contained in the aqueous solution, and the carbon dioxide component concentration is a concentration of equivalent carbon dioxide of ammonium carbamate contained in the aqueous solution.

2) The method according to 1), including:

a) a step of simultaneously measuring viscosity, density, and temperature of the aqueous solution in real time;

b) a step of determining the carbon dioxide component concentration of the aqueous solution from the viscosity and temperature measured in the step a, by use of the first correlation;

c) a step of determining the ammonia component concentration of the aqueous solution from the density and temperature measured in the step a and the carbon dioxide component concentration determined in the step b, by use of the second correlation; and d) a step of determining the water concentration from the carbon dioxide component concentration determined in the step b and the ammonia component concentration determined in the step c.

3) The method according to 2), wherein an oscillating instrument capable of measuring viscosity, density, and temperature is used in the step a.

4) A method for operating an unreacted gas absorber used in a urea production process by using the composition analysis method according to 1), including:

i) a step of measuring viscosity, density, temperature, and a flow rate of an unreacted-gas absorber outlet liquid;

ii) a step of determining carbon dioxide component concentration of the unreacted-gas absorber outlet liquid by use of the first correlation, from the viscosity and temperature measured in the step i;

iii) a step of determining ammonia component concentration of the unreacted-gas absorber outlet liquid by use of the second correlation, from the density and temperature measured in the step i and the carbon dioxide component concentration determined in the step ii;

iv) a step of determining water concentration of the unreacted-gas absorber outlet liquid from the carbon dioxide component concentration determined in the step ii and the ammonia component concentration determined in the step iii;

v) a step of finding carbon dioxide component flow rate, ammonia component flow rate, and water flow rate in the unreacted-gas absorber outlet liquid from the flow rate measured in the step i and the carbon dioxide component concentration, ammonia component concentration, and water concentration respectively determined in the steps ii to iv; and finding a water flow rate $F^{min.water}$ at which the water concentration is minimized within a range that satisfies Formula 1 and Formula 2 when only a flow rate of water in the unreacted-gas absorber outlet liquid is varied:

(Temperature measured in step $i$)+(First allowance temperature)≤(Equilibrium temperature)  Formula 1

(Solidification temperature)≤(Temperature measured in step $i$)−(Second allowance temperature)  Formula 2 wherein the equilibrium temperature in Formula 1 is an equilibrium temperature of the unreacted-gas absorber outlet liquid corresponding to the carbon dioxide component concentration, ammonia component concentration, and water concentration of the unreacted-gas absorber outlet liquid when only the water flow rate is varied, the solidification temperature in Formula 2 is a solidification temperature of the unreacted-gas absorber outlet liquid corresponding to the carbon dioxide component concentration, ammonia component concentration, and water concentration of the unreacted-gas absorber outlet liquid when only the water flow rate is varied, and each of the first and second allowance temperatures in Formulas 1 and 2 has a predetermined positive value); and vi) a step of controlling the flow rate of water fed to the unreacted gas absorber to a minimum value within a range in which the water flow rate in the unreacted-gas absorber outlet liquid is not less than $F^{min.water}$ determined in the step v.

5) The method according to 4), wherein an oscillating instrument capable of measuring viscosity, density, and temperature is used in the step i.

6) The method according to 4) or 5), wherein:

the unreacted gas absorber includes a low pressure unreacted gas absorber to which water is fed as an absorbent, and a high pressure unreacted gas absorber to which an outlet liquid from the low pressure unreacted gas absorber is fed as an absorbent;

the steps i to v are performed for each of the low pressure unreacted gas absorber and the high pressure unreacted gas absorber, so as to find:

$F_L^{min.water}$, which is the $F^{min.water}$ for the low pressure unreacted gas absorber, and $F_H^{min.water}$, which is the $F^{min.water}$ for the high pressure unreacted gas absorber; and in the step vi, the flow rate of water fed to the low pressure unreacted gas absorber is controlled to a minimum value within a range in which a water flow rate in the outlet liquid from the low pressure unreacted gas absorber is not less than $F_L^{min.water}$ and a water flow rate in an outlet liquid from the high pressure unreacted gas absorber is not less than $F_H^{min.water}$.

Advantages of the Invention

The present invention provides a method for analyzing an aqueous ammonium carbamate solution whereby the composition of the unreacted-gas absorber outlet liquid can be specified in real time, and a method for operating the unreacted gas absorber using the same.

EMBODIMENTS FOR CARRYING OUT THE INVENTION

According to the present invention, it is possible to specify the composition of an aqueous ammonium carbamate solution which is an unreacted-gas absorber outlet liquid in a urea production process. With the use of results thereof, it is possible to determine the equilibrium temperature and the solidification temperature of the solution and to control operating temperature to be optimized and the amount of water introduced into the unreacted gas absorber to a necessary minimum.

As a result of such control, it is also possible to control the total amount of water fed to a urea synthesis reactor and the stripping performance of a stripper in a stripping process, thus reducing the energy consumption of a urea plant.

The composition of the aqueous ammonium carbamate solution is specified based on the following method. The concentration of the carbon dioxide component contained in a solution containing ammonium carbamate, ammonia, and water as main components can be known from a correlation among viscosity, temperature, and carbon dioxide component concentration of the solution. Then, the ammonia component concentration can be specified from the carbon dioxide component concentration which has been known in this way, and a correlation among density, temperature, ammonia component concentration, and carbon dioxide component concentration. Here, the urea concentration can be ignored because it is low enough as mentioned above. Accordingly, the amount of water in the aqueous ammonium carbamate solution, which is the outlet liquid of the absorber, is calculated by subtracting the ammonia component concentration and the carbon dioxide component concentration from the whole.

[Analysis Object]

Figure 4:
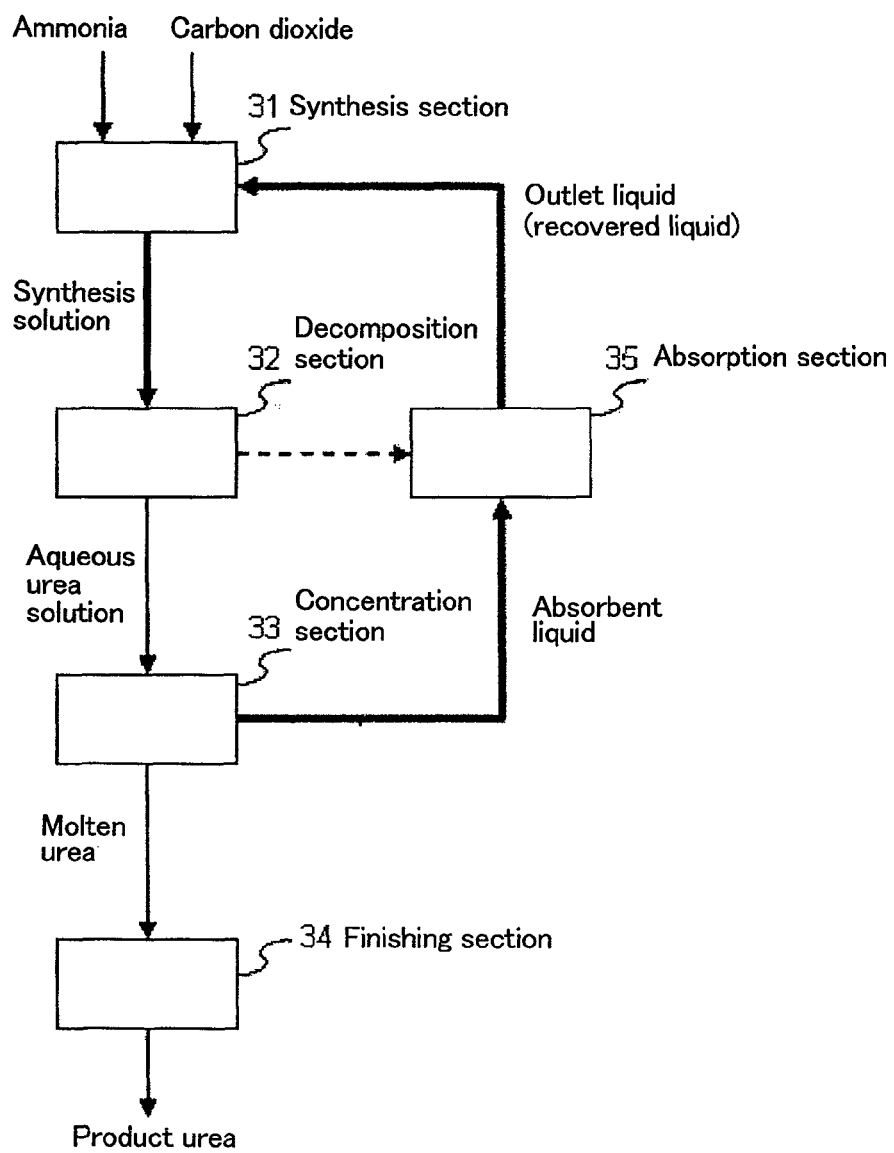
FIG. 4 is a block diagram for illustrating a urea production process.

As described above with respect to FIG. 4, the urea production process includes:

synthesis section 31 of allowing ammonia to react with carbon dioxide to synthesize urea to obtain a urea synthesis solution;

decomposition section 32 of separating unreacted ammonia and ammonium carbamate contained in the synthesis solution as a mixed gas of ammonia, carbon dioxide, and water; and absorption section 35 of feeding water to an unreacted gas absorber as an absorbent, allowing the mixed gas separated in the decomposition section to be absorbed into the absorbent, and returning an unreacted-gas absorber outlet liquid to the synthesis section 31 as a recovered liquid.

Generally, the urea production process further includes:
concentration section 33 of removing water from the remaining liquid phase (aqueous urea solution) from which the mixed gas is separated in the decomposition section to form molten urea; and finishing section 34 of cooling and solidifying the molten urea to obtain, for example, a granular product urea.

Condensed water separated in the concentration section 33 can be used as the absorbent. Further, when the absorption is performed in two stages, the unreacted-gas absorber outlet liquid in the first stage can be used as the absorbent in the unreacted gas absorber in the second stage.

In the present invention, the aqueous ammonium carbamate solution which is the unreacted-gas absorber outlet liquid in such a urea production process is the analysis object. The typical composition of the unreacted-gas absorber outlet liquid in the urea production process under normal operation is in the range of 20 to 40 mass % of the ammonia component (including ammonia excessively fed to the synthesis section and equivalent ammonia in ammonium carbamate), 20 to 42 mass % of the carbon dioxide component (equivalent carbon dioxide in ammonium carbamate), and very small amount (0 to 2 mass %) of urea, with the balance being water.

According to the present invention, it is possible to specify the ammonia component concentration, the carbon dioxide component concentration, and the water concentration of the aqueous ammonium carbamate solution in which the ammonia component concentration is 20 to 40 mass %; the carbon dioxide component concentration is 20 to 42 mass %; and the urea concentration is 0 to 2 mass %, with the balance being water. Since the urea concentration is low enough, the influence on the viscosity and density and the influence on the equilibrium temperature and the solidification temperature provided by the variation of the urea concentration are small enough and can be ignored. Further, with respect to temperature, the analysis can be performed within a conventional operation range of from 30 to 120° C.

The present invention is effective particularly in a urea production process called a stripping process. In the synthesis section in the stripping process, the urea synthesis solution from a synthesis reactor (carbon dioxide and ammonia are reacted to synthesize urea) is transferred to a stripper in the synthesis section. In the stripper, the ammonia and carbon dioxide contained in the urea synthesis solution are removed by stripping using carbon dioxide as a stripping agent at a synthesis pressure.

[Method for Analyzing Composition]

In the method for analyzing the composition of the unreacted-gas absorber outlet liquid of the present invention, the composition of the aqueous ammonium carbamate solution which is the unreacted-gas absorber outlet liquid in the urea production process, that is, the ammonia component concentration, carbon dioxide component concentration, and water concentration are determined using the first correlation and the second correlation.

First correlation: the correlation among the viscosity, the temperature, and the carbon dioxide component concentration of the aqueous ammonium carbamate solution.

Second correlation: the correlation among the density, the temperature, the ammonia component concentration, and the carbon dioxide component concentration of the aqueous ammonium carbamate solution.

In particular, the following steps a to d may be performed.
(a) The viscosity, density, and temperature of the unreacted-gas absorber outlet liquid are simultaneously measured without a time lag behind the process.
(b) The carbon dioxide component concentration of the unreacted-gas absorber outlet liquid is determined using the first correlation, from the viscosity measurement value and temperature measurement value obtained in the step a.
(c) The ammonia component concentration is determined using the second correlation, from the density and temperature obtained in the step a and the carbon dioxide component concentration determined in the step b.
(d) The water concentration is determined from the carbon dioxide component concentration determined in the step b and the ammonia component concentration determined in the step c.

Figure 1:
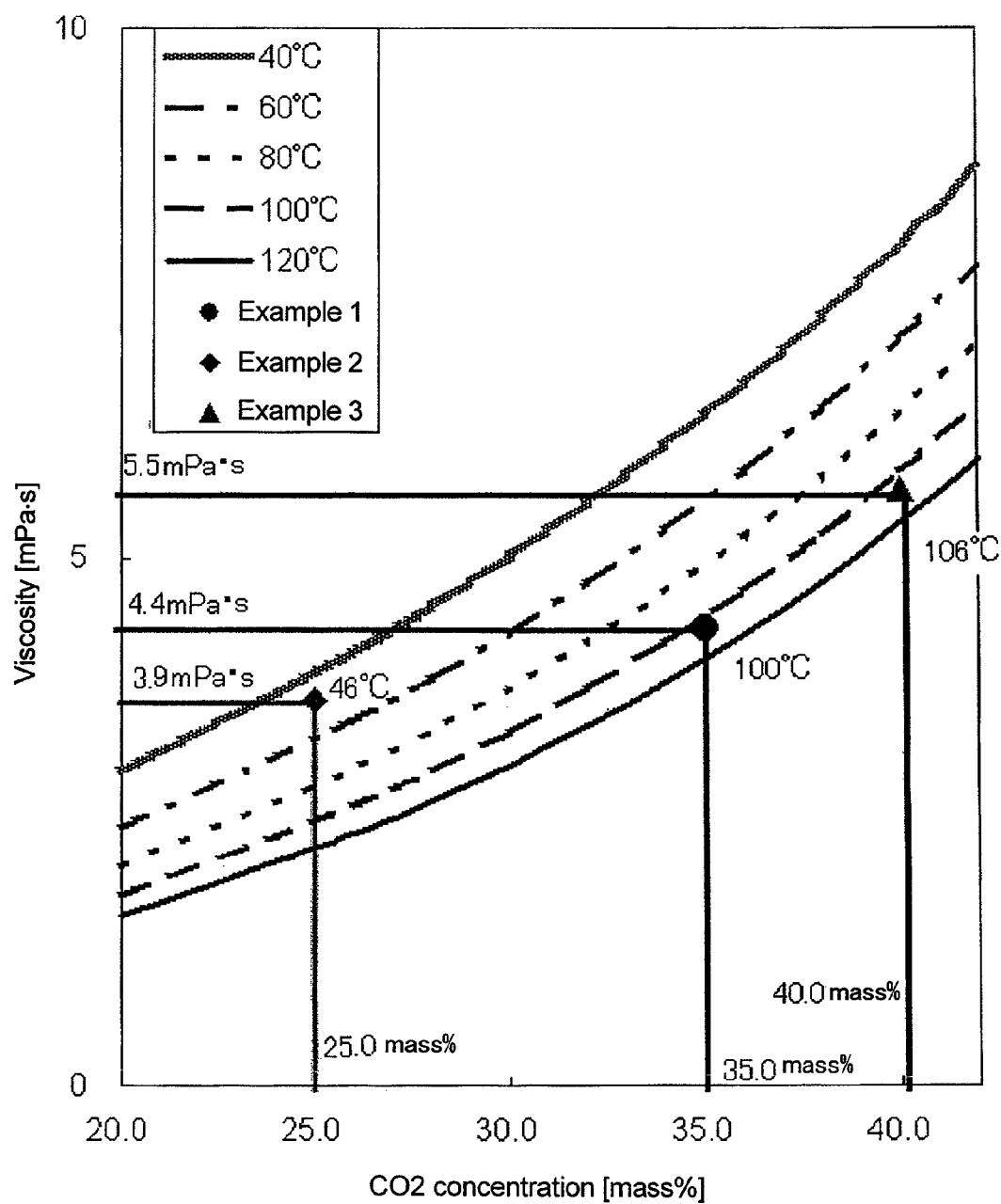
FIG. 1 is a graph showing a correlation among viscosity, temperature, and carbon dioxide component concentration of an aqueous ammonium carbamate solution.

FIG. 1 is a graph showing the correlation (first correlation) between the viscosity (mPa·s), temperature, and carbon dioxide component concentration (mass %) of the aqueous ammonium carbamate solution. The viscosity of the aqueous ammonium carbamate solution is sensitive to the carbon dioxide component concentration, and the influence from the ammonia component concentration can be ignored. Therefore, if viscosity and temperature are known, the carbon dioxide component concentration can be determined with high accuracy from the first correlation.

Figure 2:
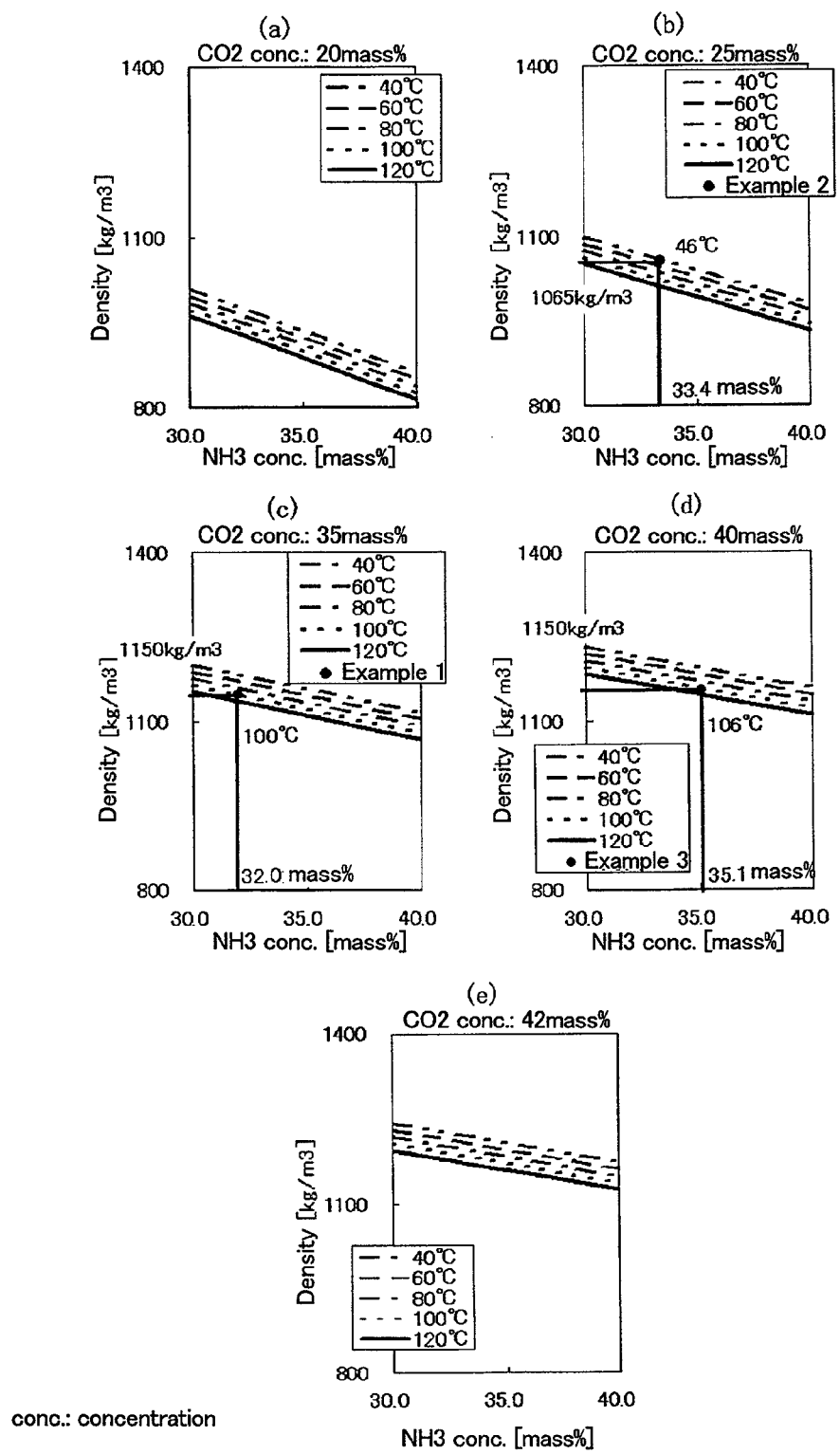
FIG. 2 is a graph for illustrating a correlation among density, temperature, ammonia component concentration, and carbon dioxide component concentration of an aqueous ammonium carbamate solution, wherein (a) to (e) are graphs respectively at carbon dioxide component concentrations of 20, 25, 35, 40, and 42 mass %.

The correlation (second correlation) among the density ($kg/m^3$), temperature (° C.), ammonia component concentration (mass %), and carbon dioxide component concentration (mass %) of the aqueous ammonium carbamate solution will be described. FIGS. 2 (a), (b), (c), (d), and (e) are graphs showing the correlation among the density, temperature, and ammonia component concentration, at carbon dioxide component concentrations of 20, 25, 35, 40, and 42 mass %, respectively. The density of the aqueous solution is sensitive to the ammonia component concentration and the carbon dioxide component concentration, and the influence from the water concentration can be ignored. Therefore, if viscosity and temperature are known and the carbon dioxide component concentration is determined as mentioned above, the ammonia component concentration can be determined from the second correlation.

Note that FIG. 1 shows the lines at temperatures of discrete values (40, 60, 80, 100, and 120° C.). When the temperature is an intermediate value (for example, 50° C.) which is not shown directly, the carbon dioxide component concentration can be determined using interpolation or extrapolation. Further, also in the case where FIG. 2 is used, interpolation or extrapolation can be used if the temperature and carbon dioxide component concentration are values which are not shown directly.

Further, since the concentration range of each component (ammonia component: 20 to 40 mass %, carbon dioxide component: 20 to 42 mass %, and urea concentration 0 to 2 mass %) and the applicable temperature range (30 to 120° C.) include the operating conditions in conventional urea plants, the correlations shown in FIGS. 1 and 2 can be used in any urea plant.

In the present invention, the equipment required for measuring the composition of the aqueous ammonium carbamate solution which is the unreacted-gas absorber outlet liquid is only a viscometer, a density meter, and a thermometer. The viscometer, density meter, and thermometer which can measure viscosity, density, and temperature in real time, respectively, are commercially available, and these instruments can be used to simultaneously measure viscosity, density, and temperature.

Further, it is preferred from the viewpoint of simplicity of analyzers to use an oscillation-type instrument in which measuring devices of a viscometer, a density meter, and a thermometer are integrated. Viscosity, density, and temperature can be simultaneously measured in real time by means of such an oscillation-type instrument. The oscillation-type instrument is commercially available, and easily available. Each of the viscometer, density meter, and thermometer or the oscillation-type instrument can perform measurement only by being installed to the inside of the unreacted gas absorber or to the inside of a pipe (particularly, an unreacted-gas absorber outlet pipe), and does not require treatment such as dilution of a sample liquid and cooling to precipitate a crystal. Therefore, it is possible to measure the composition of the absorber outlet liquid in real time. [Operating Method of the Unreacted Gas Absorber]

Examples of the method for controlling an actual plant in the present invention, particularly the method for operating an unreacted gas absorber, include the following three methods, and any of these methods may be used.

A first method is a method in which the measured values of viscosity, density, and temperature are just continuously displayed in a central control room, similarly to other instruments; an operator finds the composition of the unreacted-gas absorber outlet liquid from the correlation diagram of equilibrium temperature and solidification temperature, and the like, based on the composition of the unreacted-gas absorber outlet liquid; and, the operator optimizes the water feed rate to an unreacted gas absorber and operating conditions of the unreacted gas absorber as required. In this case, the effect of rationalization by elimination of periodical analysis of the unreacted-gas absorber outlet liquid and an improvement in operational unit requirement owing to suitable adjustment of operating conditions without a time lag can be expected.

A second method is a method in which the composition of the recovered liquid is displayed in real time on a distributed control system (hereinafter referred to as DCS) console in a central control room by mathematizing and programming the correlation among measurement results of viscosity, density, and temperature and the composition of the recovered liquid as shown in Example 1 to be described below. Further, since equilibrium temperature and solidification temperature can be estimated by simple equations if the composition is found, more useful information for an operator can be provided in real time if a function of computing the equations is added. Further, a real-time mass balance around the unreacted gas absorber can be displayed by incorporating information, from other instruments, about the water feed rate to the absorber, the flow rate of the recovered liquid, and the like. It is also possible to regularize a water feed rate, operating temperature, pressure, and the like which should be set next, from the current equilibrium vapor pressure, saturation temperature, and mass balance, and to display them on the DCS console. In this case, the operator will set the set values of controllers according to instructions displayed on the DCS console.

Thereby, a skilled operator will not be required for the operation of the absorber in the urea plant.

A third method is a case where the second method is fully automated. That is, it is a method in which the set values of the operating temperature, pressure, and the water feed rate of the absorber, or the opening of the control valves for controlling them are automatically set. In this case, the set values displayed on the DCS console in the second method may be returned as it is to the required controllers. This can create a system capable of automatically controlling the unreacted gas recovery system in an optimum state against various disturbances to the system.

Three embodiments of urea plant control have been mentioned above. All the embodiments can be carried out by only installing a viscometer, a density meter, and a thermometer, and optionally adding software. The above description assumes using DCS for the practice of the second and third methods, but a personal computer which is generally commercially available is enough to operate the required software part.

Next, an example of the absorption section of a urea production process will be described in detail with reference to FIG. 3. This figure is a flow diagram of an apparatus for performing the recovery of the aqueous ammonium carbamate solution (absorption section) by two-stage absorption using a low pressure unreacted gas absorber 1 (in FIG. 3, and hereinafter occasionally referred to as a "low pressure absorber") and a high pressure unreacted gas absorber 2 (in FIG. 3, and hereinafter occasionally referred to as a "high pressure absorber"). An outlet liquid from the high pressure unreacted gas absorber is used as a recovered and recycled liquid to the urea synthesis reactor (not shown) used in the synthesis section.

An unreacted gas flow 26 from a low pressure decomposition column (not shown) used in the decomposition section of the urea production process is fed to the low pressure unreacted gas absorber 1 which is operated at 1 to 3 $kg/cm^2G$ (0.1 to 0.3 MPaG). Water that is flow-controlled by a flow controller 8 is fed to the low pressure unreacted gas absorber 1 through a flow control valve 17, is brought into contact with the unreacted gas flow 26 as an absorbent, and absorbs ammonia and carbon dioxide. The absorbed ammonia and carbon dioxide are present in the liquid as free ammonia and ammonium carbamate. Note that G in the pressure unit means gage pressure.

The low pressure absorber 1 has, for example, a structure of a shell and tube heat exchanger, and the heat of reaction and the heat of absorption accompanying absorption are removed by cooling water passing through the tubes. The flow rate of the cooling water is controlled by a temperature controller 11 and a temperature control valve 19 so that the temperature of the liquid in the low pressure absorber is kept at a constant value in the range of about 30° C. to 60° C.

The pressure of the low pressure unreacted gas absorber 1 is kept constant by adjusting the gas volume released from a pressure control valve 18 by a pressure controller 9.

A low pressure recovered liquid (an outlet liquid from the low pressure unreacted-gas absorber) that has absorbed unreacted gas is boosted in pressure by a pump 20 and fed to the high pressure unreacted gas absorber 2 through a flow control valve 21. By adjusting the flow rate of the low pressure recovered liquid by the flow control valve 21, the liquid level of the low pressure unreacted gas absorber 1 is controlled by cascade control that determines a set value of a flow controller 12 from a liquid level controller 10.

The viscosity, density, and temperature of the low pressure recovered liquid are measured by a viscosity/density/temperature meter 28, and these measured values are transmitted to a control system 7. As the viscosity/density/temperature meter 28, an oscillation-type instrument provided with a thermometer is preferably used.

On the other hand, an unreacted gas flow 27 from a high pressure decomposition column (not shown) used in the decomposition section of the urea production process is transferred to the high pressure unreacted gas absorber 2 operated at 15 to 20 $kg/cm^2G$ (1.5 to 2.0 MPaG). In the high pressure unreacted gas absorber 2, the recovered liquid which is transferred from the low pressure unreacted gas absorber and boosted in pressure by the pump 20 is brought into contact with the unreacted gas flow 27 as an absorbent and absorbs ammonia and carbon dioxide. The absorbed ammonia and carbon dioxide are present as free ammonia and ammonium carbamate in the high pressure recovered liquid (outlet liquid from the high pressure unreacted gas absorber).

The high pressure unreacted gas absorber 2 has, for example, a structure of a shell and tube heat exchanger, and the heat of reaction and the heat of absorption accompanying absorption are removed by cooling water passing through the tubes. The flow rate of the cooling water is controlled by a temperature controller 15 and a temperature control valve 23 so that the temperature in the high pressure absorber is kept at a constant value in the range of 80° C. to 120° C.

The pressure of the high pressure unreacted gas absorber 2 is kept constant by adjusting the gas volume released from a pressure control valve 22 by a pressure controller 13.

The high pressure recovered liquid that has absorbed unreacted gas is boosted in pressure by a pump 25 and transferred to the urea synthesis reactor used in the synthesis section through a flow control valve 24. The liquid level of the high pressure absorber 2 is controlled by cascade control that determines a set value of a flow controller 16 through a liquid level controller 14.

The viscosity, density, and temperature of the high pressure recovered liquid (outlet liquid from the high pressure unreacted gas absorber) obtained from the high pressure unreacted gas absorber 2 are measured by a viscosity/density/temperature meter 29 and sent to the control system 7. As the viscosity/density/temperature meter 29, an oscillation-type instrument provided with a thermometer is preferably used.

The control system 7 receives, for each absorber, the pressure, the feed rate of water as an absorbent, and the viscosity, density and temperature of the recovered liquid, among the variables related to the high pressure unreacted gas absorber 2 and the low pressure unreacted gas absorber 1, and determines the composition of each recovered liquid. Further, the control system 7 calculates equilibrium temperature and solidification temperature from the determined composition and pressure, for each absorber. At this time, with respect to the composition of the recovered liquid, the carbon dioxide concentration is specified from the correlation among the measured viscosity and temperature, and the carbon dioxide component concentration, and the ammonia component concentration is specified from the correlation among the density, temperature, carbon dioxide component concentration, and ammonia component concentration. Further, for each of the high pressure unreacted gas absorber 2 and the low pressure unreacted gas absorber 1, the control system 7 determines, outputs, and feeds back to the controllers a new and optimum set value for the amount of water as an absorbent, based on the recovered liquid composition determined in this way, and the equilibrium temperature and solidification temperature, the temperature, the pressure, and the feed rate of water as an absorbent.

Here, there has been shown an example in which two unreacted gas flows are fed to a low-pressure and high-pressure unreacted gas absorbers from the decomposition section and subjected to two-stage absorption in the low-pressure and high-pressure absorbers in the absorption section, but the present invention is not limited to this example. Only one unreacted gas flow may be sent to the absorption section from the decomposition section and subjected to single-stage absorption in the absorption section. When the size of the absorber is limited, such as in a case where the production volume of the plant is large or in a case of revamping, the absorbers may be installed in parallel in the same stage. The absorbers may be installed in three stages or more.

EXAMPLES

Example 1

Figure 5:
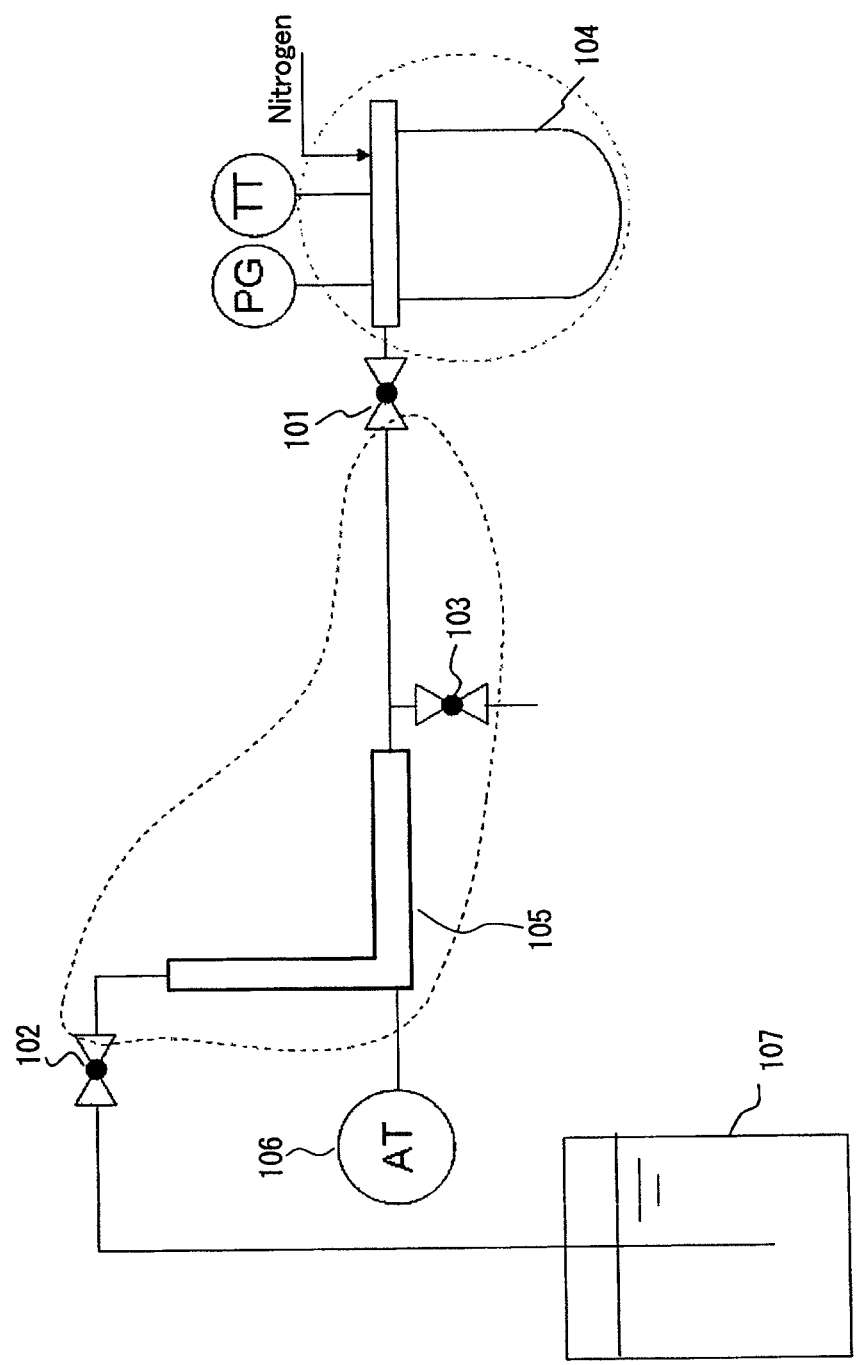
FIG. 5 is a schematic diagram for illustrating a measuring device used in Examples.

First, there will be described a method for finding the correlation among the viscosity and temperature of the unreacted-gas absorber outlet liquid and the carbon dioxide component concentration in the same liquid, and the correlation among the density and temperature of the unreacted-gas absorber outlet liquid and the ammonia component concentration and the carbon dioxide component concentration in the same liquid. An aqueous solution simulating the unreacted-gas absorber outlet liquid was measured for the viscosity, density, temperature, ammonia component concentration, carbon dioxide component concentration, and water concentration by use of the apparatus shown in FIG. 5. The measurement was performed according to the following procedures. Note that the parts surrounded by dashed lines in FIG. 5 are parts where temperature is controlled by an electric heater.

Required amounts of water, ammonium hydrogen carbonate, and ammonia are introduced into an autoclave 104 in this order, respectively based on the target composition.

The inlet and outlet valves of the autoclave are completely closed to separate the autoclave, which is then heated by an electric heater installed outside the autoclave. Subsequently, the autoclave contents are stirred until the temperature inside the autoclave reaches a steady state at a target temperature. At this time, ammonia and carbon dioxide are vaporized with the increase in temperature, and the pressure in the autoclave spontaneously increases. Further, the amounts of ammonia and carbon dioxide to be vaporized are minimized to prevent the change in the liquid composition due to evaporation, by determining the liquid volume so that the liquid height inside the autoclave will be high enough. The autoclave is provided with a pressure gauge (PG) and a thermometer (TT).

Each of the autoclave 104 and a flow-through chamber 105 is pressurized with nitrogen to prevent the evaporation of ammonia and carbon dioxide at the time of transferring the liquid.

A valve 101 is opened to introduce the liquid into the flow-through chamber. A valve 103 is closed at this time.

A valve 102 is operated to discharge the gas inside the flow-through chamber to completely immerse a viscosity/density/temperature meter 106 in the liquid.

The viscosity, density, and temperature are measured after the indications of the viscosity/density/temperature meter 106 are stabilized.

The intensity of the heater is changed after the measurement, and the liquid is left as it stands until the temperature reaches a steady state again at another target temperature.

The viscosity, density, and temperature are measured after the indications of the viscosity/density/temperature meter 106 are stabilized. The liquid composition is not changed, but the temperature increase and the steady state are repeated, and the viscosity, density, and temperature are measured at each temperature.

The valve 101 is closed and the valve 103 is opened to collect the solution to quantify the concentrations of the ammonia component, carbon dioxide component, and water by a chemical analysis.

An oscillation-type instrument "Emerson-Solartron process density and viscosity meter" (trade name) was used as the viscosity/density/temperature meter. The ammonia component concentration is specified by back titration using sulfuric acid and sodium hydroxide. Further the carbon dioxide component concentration is specified by back titration using hydrochloric acid and sodium hydroxide.

Further, the fluid discharged from the flow-through chamber is introduced into an exhaust ammonia absorber 107, where ammonia in the fluid is absorbed.

In the method as described above, there were prepared aqueous solutions in which the ammonia component concentration was 20 to 40 mass %; the carbon dioxide component concentration was 20 to 42 mass %; and the urea concentration was 0 to 2 mass %, with the balance being water, which is the typical composition of the absorber outlet liquid in the urea production process.

The correlation (first correlation) between the viscosity, temperature, and carbon dioxide component concentration which were measured as described above for each of the prepared aqueous solutions is shown in FIG. 1. In FIG. 1, the ordinate represents viscosity (mPa·s), and the abscissa represents the carbon dioxide component concentration (mass %). Further, the correlation among the density, temperature, and ammonia component concentration which were measured as described above for each aqueous solution is shown in FIG. 2 (a) to (e), for every carbon dioxide component concentration. In FIG. 2, the ordinate represents density ($kg/cm^3$), and the abscissa represents the ammonia component concentration (mass %).

When the unreacted-gas absorber outlet liquid in an actual urea production plant was sampled and measured, the viscosity was 4.4 mPa·s and the density was 1150 $kg/m^3$ at a temperature of 100° C.

From the correlation in FIG. 1, the carbon dioxide component concentration was determined to be 35.0 mass %. On the other hand, when the concentration of the carbon dioxide component in the same sample solution was quantified by a chemical analysis, it was 35.1 mass %, which was well in agreement with the above determined value.

From the correlation shown in FIG. 2 (c) and the carbon dioxide component concentration determined as described above, it was possible to determine that the ammonia component concentration was 32.0 mass %. On the other hand, when the concentration of the ammonia component in the same sample solution was quantified by a chemical analysis, it was 32.2 mass %, which was well in agreement with the above determined value.

Further, since the urea concentration in the absorption section is low enough as described above, the influence of the variation of the urea concentration on the viscosity and density and the influence on the equilibrium temperature and solidification temperature are small enough and can be ignored. The water concentration can be calculated by subtracting the ammonia component concentration and the carbon dioxide component concentration from the whole. That is, the water concentration is specified to be 33.0 (=100−35.0−32.0) mass %.

Example 2

Figure 3:
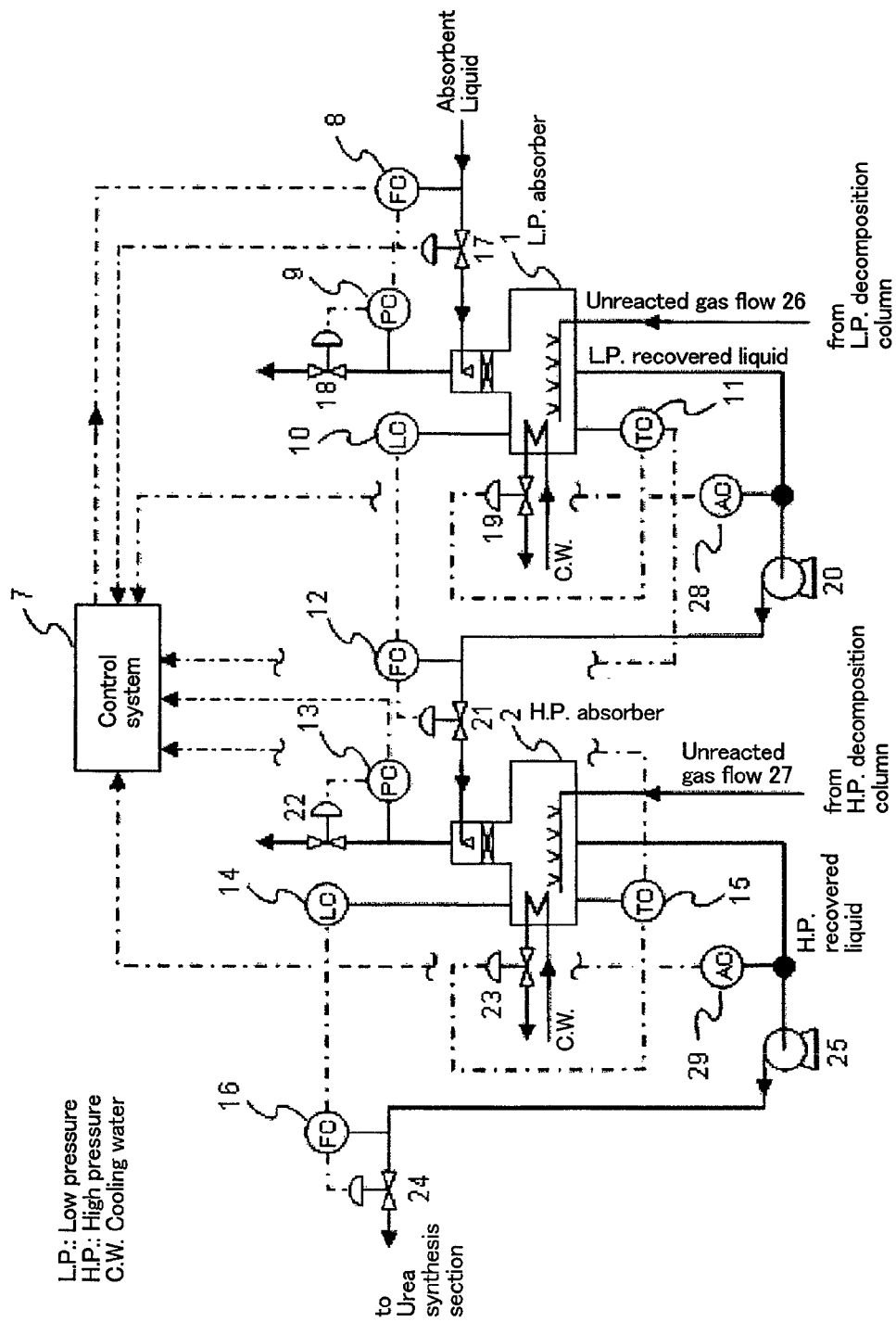
FIG. 3 is a flow diagram for illustrating an absorption section of a urea production process.

FIG. 3 is a diagram in the case where low pressure and high pressure absorbers are installed in two stages, and shows a process flow in which the water separated in the concentration section is fed to the low pressure absorber as an absorbent and an outlet liquid from the low pressure absorber is used as an absorbent fed to the high pressure absorber. The absorber may be installed in a single stage or in two stages as described above. In the present Example, the optimization of the operating conditions of the absorption section was attempted in the case where only the low pressure absorber was installed in the urea production plant. Specifically, in the low pressure absorption section, a facility including a single-stage low pressure absorber was used, which has a configuration (valve 21 is included, but valve 24 is not included) excluding the configuration around the high pressure absorber from after the valve 21 to the valve 24 in the configuration shown in FIG. 3. When the low pressure absorber is used in a single stage, water used as an absorbent is allowed to absorb ammonia and carbon dioxide in the absorption section, and since the high pressure absorber is not installed, the recovered liquid from the valve 21 is directly returned to the synthesis section. The absorbent used here contains a small amount of urea because water separated in the concentration section is used as the absorbent.

The process variables around the low pressure unreacted gas absorber 1 at a certain time were as follows:
operating pressure (instrument reading of the pressure controller 9): 2.4 kg/cm$^2$G (0.24 MPaG),
operating temperature (instrument reading temperature of the viscosity/density/temperature meter 28): 46° C.,
absorbent feed rate (set value of the flow controller 8): 10.3 t/h,
viscosity (instrument reading viscosity of the viscosity/density/temperature meter 28): 3.9 mPa·s,
density (instrument reading density of the viscosity/density/temperature meter 28): 1065 kg/m$^3$, and
flow rate of the outlet liquid from the low pressure unreacted gas absorber (recovered liquid): 38.6 t/h.

An oscillation-type instrument "Emerson-Solartron process density and viscosity meter" (trade name) was used as the viscosity/density/temperature meter, and the viscosity, density, and temperature of the outlet liquid from the low pressure unreacted gas absorber are simultaneously measured in real time. Further, the flow rate of the outlet liquid from the low pressure unreacted gas absorber is also measured simultaneously with these measurements by a flow meter (step a or i).

The carbon dioxide component concentration was determined from the correlation (FIG. 1) between the carbon dioxide composition in ammonium carbamate, viscosity, and temperature of the outlet liquid from the low pressure unreacted gas absorber (step b or ii). Next, the ammonia component concentration was found from this carbon dioxide component concentration and the correlation (FIG. 2(b)) between the ammonia component concentration, carbon dioxide component concentration, density, and temperature (step c or iii). Since the urea concentration in the absorption section is low enough, the influence of the variation of the urea concentration on the viscosity and density and on the equilibrium temperature and solidification temperature are small enough and can be ignored. The water concentration can be calculated by subtracting the ammonia component concentration and the carbon dioxide component concentration from the whole (step d or iv). As a result, the composition of the recovered liquid was as shown in the following table.

In Tables 1 to 4, NH$_3$ means the ammonia component, CO$_2$ means the carbon dioxide component, and the unit of the component flow rate is t/h.

Note that the flow rate of each component (carbon dioxide component flow rate, ammonia component flow rate, and water flow rate) is found in step v from the flow rate of the outlet liquid from the low pressure unreacted gas absorber measured in the step i and the carbon dioxide component concentration, ammonia component concentration, and water concentration determined in the steps ii to iv, respectively. The flow rate of each component is also shown in Table 1.

TABLE 1

|  | mass % | C.F.R. |
|---|---|---|
| NH3 | 33.4 | 12.89 |
| CO2 | 25.0 | 9.65 |
| H2O | 41.6 | 16.06 |

C.F.R.: Component Flow Rate

The equilibrium temperature and solidification temperature of the aqueous ammonium carbamate solution having the above composition are found to be 54° C. and 29° C., respectively (here, it is possible to judge whether it is necessary to adjust the flow rate of water or not, by finding the equilibrium temperature and solidification temperature). Here, the equilibrium temperature is determined according to the Gibbs' phase rule, since the composition and pressure have already been found. The solidification temperature is similarly determined from the known composition.

When focusing attention on the equilibrium temperature, since there is a difference of 8° C. between the operating temperature (46° C.) and the equilibrium temperature (54° C.), it is possible to judge that the amount of water as an absorbent in the outlet liquid from the low pressure unreacted gas absorber is excessive. On the other hand, when focusing attention on the solidification temperature, since there is a difference of 17° C. between the operating temperature (46° C.) and the solidification temperature (29° C.), it is possible to judge that the amount of water in the outlet liquid from the low pressure unreacted gas absorber can be reduced.

Since it is preferred to reduce water concentration as far as possible while the differences from the operating temperature are ensured, a composition and component flow rates were determined as described in the following table. They were determined by varying (reducing) only the amount of water without changing the operating pressure so that the equilibrium temperature will be 51° C. or more (allowance from the operating temperature is 5° C.), and the solidification temperature will be 41° C. or less (allowance from the operating temperature is 5° C.). In this case, the equilibrium temperature is 51° C., and the solidification temperature is 34° C.

That is, from the component flow rates shown in Table 1, only the water flow rate of the outlet liquid from the low pressure unreacted gas absorber was varied to determine the water flow rate $F^{min.water}$ at which the water concentration is the minimum in the range represented by Formula 1 and Formula 2. As a result, it was determined to be 14.50 t/h (step v).

(Temperature measured in step $i$)+(First allowance temperature)≤(Equilibrium temperature)　　　　Formula 1

(Solidification temperature)≤(Temperature measured in step $i$)−(Second allowance temperature)　　　　Formula 2

The equilibrium temperature in Formula 1 is the equilibrium temperature of the unreacted-gas absorber outlet liquid corresponding to the carbon dioxide component concentration, ammonia component concentration, and water concentration of the unreacted-gas absorber outlet liquid when only the water flow rate is varied;

the solidification temperature in Formula 2 is the solidification temperature of the unreacted-gas absorber outlet liquid corresponding to the carbon dioxide component concentration, ammonia component concentration, and water concentration of the unreacted-gas absorber outlet liquid when only the water flow rate is varied; and each of the first and the second allowance temperature in Formulas 1 and 2 has a predetermined positive value.

Note that each of the first and second allowance temperatures is used for absorbing measurement accuracy of instruments and sudden changes of operating conditions. These allowance temperatures may be reset while watching actual operating status, but they may usually be about 5° C. The same can generally be said with respect to the operation of an unreacted gas absorber regardless of whether it is a low pressure absorber or a high pressure absorber.

TABLE 2

|      | mass % | C.F.R. |
|------|--------|--------|
| NH3  | 34.8   | 12.89  |
| CO2  | 26.1   | 9.65   |
| H2O  | 39.1   | 14.50  |

In order to obtain this composition, the flow rate of water in the recovered liquid should be set to 14.50 t/h. Therefore, a set value of the flow rate controller 8 to be newly set will be 10.3−(16.06−14.50)=8.74 t/h. That is, the flow rate of water fed to the low pressure unreacted gas absorber, which is the minimum in the range in which the flow rate of water in the outlet liquid from the low pressure unreacted gas absorber is the above-described $F^{min.water}$ (14.50 t/h) or more, is 8.74 t/h. Therefore, the flow rate of water fed to the low pressure unreacted gas absorber is controlled to this value (step vi).

The smaller the amount of water in the system is, the more the synthetic reaction of urea proceeds. Therefore, the effect that, for example, the urea synthesis rate in the synthesis section is improved by 1.0% and the steam consumption in the whole urea plant per 1 t of urea production is reduced by 1.5% can be expected by the reduction in the water feed rate of 1.56 t/h.

By using the logic as described above, it was possible to optimize the operating conditions of the unreacted gas absorber of the urea production process based on the measured values of viscosity, density, and temperature.

Example 3

In the present Example, the optimization of the operating conditions of the absorption section was attempted in the case where only the high pressure absorber was installed in the urea production plant. In the absorption section, a facility including a single-stage high pressure absorber was used, which has a configuration (valve 17 is included, but valve 21 is not included) excluding the configuration around the low pressure absorber from after the valve 17 to the valve 21 in the configuration shown in FIG. 3. When the high pressure absorber is used in a single stage, since the low pressure absorber does not present, the water used as an absorbent which is directly fed to the high pressure absorber from the concentration system through the valve 17 is caused to absorb ammonia and carbon dioxide and then returned to the synthesis section. The absorbent used here contains a small amount of urea because the water separated in the concentration section is used as the absorbent.

The process variables around the high pressure absorber 2 at a certain time were as follows:

operating pressure (instrument reading of the pressure controller 13): 15.8 kg/cm²G (1.55 MPaG), operating temperature (instrument reading temperature of the viscosity/density/temperature meter 29): 106° C., absorbent liquid feed rate (set value of the flow controller 8): 10.39 t/h, viscosity (instrument reading viscosity of the viscosity/density/temperature meter 29): 5.5 mPa·s, density (instrument reading density of the viscosity/density/temperature meter 29): 1150 kg/m³, flow rate of the outlet liquid from the high pressure unreacted gas absorber (instrument reading of the flow controller 16): 81.31 t/h.

An oscillation-type instrument "Emerson-Solartron process density and viscosity meter" (trade name) was used as the viscosity/density/temperature meter, to simultaneously measure the viscosity, density, and temperature of the outlet liquid from the high pressure unreacted gas absorber in real time. Further, the flow rate of the outlet liquid from the high pressure unreacted gas absorber is also measured simultaneously with these measurements by a flow meter (step a or i).

On the other hand, the carbon dioxide component concentration was determined from the correlation (FIG. 1) between the carbon dioxide component concentration and viscosity of the outlet liquid (high pressure recovered liquid) from the high pressure unreacted gas absorber (step b or ii). Next, the ammonia component concentration was found from this carbon dioxide component concentration and the correlation (FIG. 2(*d*)) between the ammonia component concentration, carbon dioxide component concentration, density, and temperature (step c or iii). Since the urea concentration in the absorption section is low enough, the influence of the variation of the urea concentration on the viscosity and density and on the equilibrium temperature and solidification temperature are small enough and can be ignored. The water concentration can be calculated by subtracting the ammonia component concentration and the carbon dioxide component concentration from the whole (step d or iv). As a result, the composition of the outlet liquid from the high pressure unreacted gas absorber was as shown in the following table.

Note that the flow rate of each component (carbon dioxide component flow rate, ammonia component flow rate, and water flow rate) is found in the step v from the flow rate of the outlet liquid from the high pressure unreacted gas absorber measured in the step i and the carbon dioxide component concentration, ammonia component concentration, and water concentration determined in the steps ii to iv, respectively. The flow rate of each component is also shown in Table 3.

TABLE 3

|      | mass % | C.F.R. |
|------|--------|--------|
| NH3  | 35.1   | 28.54  |
| CO2  | 40.0   | 32.52  |
| H2O  | 24.9   | 20.25  |

The equilibrium temperature and solidification temperature of the aqueous ammonium carbamate solution having the above composition are found to be 112° C. and 92° C., respectively (here, it is possible to judge whether it is necessary to adjust the flow rate of water or not, by finding the equilibrium temperature and solidification temperature). Since there is a difference of 6° C. between the operating temperature (106° C.) and the equilibrium temperature (112° C.), and there is a difference of 14° C. between the operating temperature (106° C.) and the solidification temperature (92° C.), it is possible to judge that the amount of water in the outlet liquid from the high pressure unreacted gas absorber can be reduced.

Since it is preferred to reduce water concentration as far as possible, a composition was determined as described in the following table. This composition was determined by reducing only the amount of water so that the equilibrium temperature will be 111° C. or more (allowance from the operating temperature is 5° C.), and the solidification temperature will be 101° C. or less (allowance from the operating temperature is 5° C.) without changing the operating pressure. In this case, the equilibrium temperature is 111° C., and the solidification temperature is 100° C.

That is, from the component flow rates shown in Table 3, only the water flow rate of the outlet liquid from the high pressure unreacted gas absorber was varied to find the water flow rate $F^{min.water}$ at which the water concentration is the minimum in the range represented by Formula 1 and Formula 2 mentioned above. As a result, it was determined to be 18.40 t/h (step v).

TABLE 4

|  | mass % | C.F.R. |
|---|---|---|
| NH3 | 35.9 | 28.54 |
| CO2 | 40.9 | 32.52 |
| H2O | 23.2 | 18.40 |

In order to obtain this composition, the flow rate of water in the outlet liquid from the high pressure unreacted gas absorber should be set to 18.40 t/h. Therefore, a set value of the flow controller 8 to be newly set will be 10.39−(20.25−18.40)=8.54 t/h. That is, the flow rate of water fed to the high pressure unreacted gas absorber, which is the minimum in the range in which the flow rate of water in the outlet liquid from the high pressure unreacted gas absorber is the $F^{min.water}$ (18.40 t/h) or more, is 8.54 t/h. Therefore, the flow rate of water fed to the high pressure unreacted gas absorber is controlled to this value (step vi).

By using the logic as described above, it was possible to optimize the operating conditions of the unreacted gas absorber of the urea production process based on the measured values of viscosity, density, and temperature.

The smaller the amount of water in the system is, the more the synthetic reaction of urea proceeds. Therefore, the effect that, for example, the urea synthesis rate in the synthesis section is improved by 1.0% and the steam consumption in the whole urea plant per 1 t of urea production is reduced by 1.5% can be expected by the reduction in the water feed rate of 1.85 t/h.

As described above, according to the present invention, the composition of the aqueous ammonium carbamate solution can be quickly measured by measuring the viscosity, density, and temperature thereof. That is, the composition of the unreacted-gas absorber outlet liquid can be directly specified in real time from the density, temperature, and viscosity. As a result, the effects to be described below can also be obtained.

Example 4

The optimization of the operating conditions of the absorption section was attempted in the case where the low pressure absorber and the high pressure absorber were successively installed in two stages in the urea production plant. In the absorption section, the absorption facility having a configuration shown in FIG. 3 was used. The water used as an absorbent which is fed from the concentration system is allowed to absorb ammonia and carbon dioxide and then returned to the synthesis section. Since the water separated in the concentration section is used here as the absorbent, it contains a small amount of urea. When the absorbers are installed in two stages, water is fed to the low pressure absorber as the absorbent, and the outlet liquid from the low pressure absorber is fed to the high pressure absorber as the absorbent. Accordingly, the amount of water fed as the absorbent is determined such that the amount necessary for the low pressure absorber is compared with the amount necessary for the high pressure absorber, and one having a not-smaller value is selected between them. Thus, a necessary amount of water is fed by the flow controller 8.

The process variables around the low pressure unreacted gas absorber 1 and the high pressure unreacted gas absorber 2 at a certain time were the same as those of Examples 2 and 3, respectively. However, since water to the absorption section was fed only to the low pressure unreacted gas absorber, the feed rate of water was 10.3 t/h, which was the same as in Example 2.

As found in Examples 3 and 4, the flow rate of water in the outlet liquid from the low pressure unreacted gas absorber should be set to 14.50 t/h, and the flow rate of water in the outlet liquid from the high pressure unreacted gas absorber should be set to 18.40 t/h. The feed rate of water which is needed for each absorber will be as follows: 10.3−(16.06−14.50)=8.74 t/h for the low pressure unreacted gas absorber, and 10.3−(20.25−18.40)=8.45 t/h for the high pressure unreacted gas absorber. A set value of the flow controller 8 to be newly set is a value which is not smaller of these, that is, 8.74 t/h.

By using the logic as described above, it was possible to optimize the operating conditions of the unreacted gas absorbers of the urea production process based on the measured values of viscosity, density, and temperature.

The smaller the amount of water in the system is, the more the synthetic reaction of urea proceeds. Therefore, the effect that, for example, the urea synthesis rate in the synthesis section is improved by 1.0% and the steam consumption in the whole urea plant per 1 t of urea production is reduced by 1.5% can be expected by the reduction in the water feed rate of 1.6 t/h.

As a result of using the analytical method as described above, the following effects can be expected.

Since the composition of the unreacted-gas absorber outlet liquid (recovered liquid) can be known in real time, the feedback is remarkably quickly given to operation as compared with the analysis through the conventional sample collection. As a result, the integrated value of the deviations from the optimum operating conditions is remarkably small, and the content of water in the recovered liquid can be controlled to a value closer to the minimum. These results lead to the improvement in the urea conversion of the urea synthesis reactor and reduction in the energy consumption of the urea production plant.

For example, the synthesis rate of the synthesis reactor can be increased by 1 to 2%, and the energy consumption of the urea plant can be reduced by 1 to 2%. Further, variations of operation can be instantaneously known from the results of the measurement, and the losses of ammonia and carbon dioxide can be reduced by always keeping the absorption performance at a level close to the optimum.

Since the composition of the recovered liquid can be always monitored with the viscosity, density, and temperature, the analysis through sample collection and the personnel for it are not required, thereby achieving rationalization.

It is possible to use an industrial measurement device for simultaneously measuring viscosity, density, and temperature, which is inexpensive and excellent in durability as compared with a refractometer or the like. That is excellent in terms of maintenance and cost.

When, for example, an oscillating instrument is used as such a measurement device, it is not necessary to use a dilution device which is required for measuring electric conductivity, a cooling device which is required for using a photometer, and a colorimetric analyzer which is required for performing analysis by a colorimetric method. Thus, the complication of measuring devices can be avoided.

By adding simple software, it is possible to display, in real time, the composition, equilibrium temperature, and solidification temperature of the recovered liquid, and the mass balance around the unreacted gas absorber, and it is possible to provide much information useful for operators. Further, operators can be instructed by programming and incorporating a rule for determining the optimum set value of each controller based on such information. Thereby, the optimum operation can be performed even by an operator who is not skillful. Furthermore, if the set value which can be determined by the rule is automatically fed back to each controller, fully automatic optimization of operation can be achieved without participation of a human with respect to disturbances to the unreacted gas absorber.

Since the logic of the software is simple and the data volume is small, it can be installed also on a commercially available personal computer.

DESCRIPTION OF THE SYMBOLS

1 Low pressure unreacted gas absorber
2 High pressure unreacted gas absorber
7 Control system
8 Flow controller
9 Pressure controller
10 Liquid level controller
11 Temperature controller
12 Flow controller
13 Pressure controller
14 Liquid level controller
15 Temperature controller
16 Flow controller
17 Flow control valve
18 Pressure control valve
19 Temperature control valve
20 Pump
21 Flow control valve
22 Pressure control valve
23 Temperature control valve
24 Flow control valve
25 Pump
26 Low pressure unreacted gas flow ($NH_3$—$CO_2$—$H_2O$ mixed gas flow)
27 High pressure unreacted gas flow ($NH_3$—$CO_2$—$H_2O$ mixed gas flow)
28 Viscosity/density/temperature meter
29 viscosity/density/temperature meter
31 Synthesis section
32 Decomposition section
33 Condensation section
34 Finishing section
35 Absorption section
101, 102, and 103 Valve
104 Autoclave
105 Flow-through chamber
106 Viscometer, density meter, and thermometer
107 Exhaust ammonia absorber

The invention claimed is:

1. A composition analysis method for analyzing composition of an aqueous solution of ammonium carbamate, the aqueous solution being an unreacted-gas absorber outlet liquid in an absorption section of a urea production process, comprising:
    determining ammonia component concentration, carbon dioxide component concentration, and water concentration of the aqueous solution of ammonium carbamate by using a first correlation which is a correlation among viscosity, temperature, and carbon dioxide component concentration of the aqueous solution, and a second correlation which is a correlation among density, temperature, ammonia component concentration, and carbon dioxide component concentration of the aqueous solution,
    wherein the ammonia component concentration is a concentration of a sum of free ammonia and equivalent ammonia of ammonium carbamate which are contained in the aqueous solution, and
    the carbon dioxide component concentration is a concentration of equivalent carbon dioxide of ammonium carbamate contained in the aqueous solution.

2. The method according to claim 1, comprising:
    a) a step of simultaneously measuring viscosity, density, and temperature of the aqueous solution in real time;
    b) a step of determining the carbon dioxide component concentration of the aqueous solution from the viscosity and temperature measured in step a, by use of the first correlation;
    c) a step of determining the ammonia component concentration of the aqueous solution from the density and temperature measured in step a and the carbon dioxide component concentration determined in step b, by use of the second correlation; and
    d) a step of determining the water concentration from the carbon dioxide component concentration determined in step b and the ammonia component concentration determined in step c.

3. The method according to claim 2, wherein an oscillating instrument capable of measuring viscosity, density, and temperature is used in step a.

4. A method for operating an unreacted gas absorber used in an absorption section of a urea production process, by use of the composition analysis method according to claim 1, comprising:
    i) a step of measuring viscosity, density, temperature, and a flow rate of an unreacted-gas absorber outlet liquid;
    ii) a step of determining carbon dioxide component concentration of the unreacted-gas absorber outlet liquid by use of the first correlation, from the viscosity and temperature measured in step i;
    iii) a step of determining ammonia component concentration of the unreacted-gas absorber outlet liquid by use of the second correlation, from the density and temperature measured in step i and the carbon dioxide component concentration determined in step ii;
    iv) a step of determining water concentration of the unreacted-gas absorber outlet liquid from the carbon dioxide component concentration determined in step ii and the ammonia component concentration determined in step iii;

v) a step of finding carbon dioxide component flow rate, ammonia component flow rate, and water flow rate in the unreacted-gas absorber outlet liquid from the flow rate measured in step i and the carbon dioxide component concentration, ammonia component concentration, and water concentration respectively determined in steps ii to iv, and finding a water flow rate $F^{min.water}$ at which the water concentration is minimized within a range that satisfies Formula 1 and Formula 2 when only a water flow rate in the unreacted-gas absorber outlet liquid is varied:

(Temperature measured in step $i$)+(First allowance temperature)≤(Equilibrium temperature)    Formula 1

(Solidification temperature)≤(Temperature measured in step $i$)−(Second allowance temperature)    Formula 2 wherein the equilibrium temperature in Formula 1 is an equilibrium temperature of the unreacted-gas absorber outlet liquid, corresponding to the carbon dioxide component concentration, ammonia component concentration, and water concentration of the unreacted-gas absorber outlet liquid when only the water flow rate is varied, the solidification temperature in Formula 2 is a solidification temperature of the unreacted-gas absorber outlet liquid, corresponding to the carbon dioxide component concentration, ammonia component concentration, and water concentration of the unreacted-gas absorber outlet liquid when only the water flow rate is varied, and each of the first and second allowance temperatures in Formulas 1 and 2 has a predetermined positive value; and vi) a step of controlling a flow rate of water fed to the unreacted gas absorber to a minimum value within a range in which a water flow rate in the unreacted-gas absorber outlet liquid is not less than $F^{min.water}$ determined in step v.

5. The method according to claim 4, wherein an oscillating instrument capable of measuring viscosity, density, and temperature is used in step i.

6. The method according to claim 4, wherein
the unreacted gas absorber includes a low pressure unreacted gas absorber to which water is fed as an absorbent, and a high pressure unreacted gas absorber to which an outlet liquid from the low pressure unreacted gas absorber is fed as an absorbent;
steps i to v are performed for each of the low pressure unreacted gas absorber and the high pressure unreacted gas absorber, so as to find:
$F_L^{min.water}$, which is $F^{min.water}$ for the low pressure unreacted gas absorber, and
$F_H^{min.water}$, which is $F^{min.water}$ for the high pressure unreacted gas absorber; and
in step vi, the flow rate of water fed to the low pressure unreacted gas absorber is controlled to a minimum value within a range in which a water flow rate in the outlet liquid from the low pressure unreacted gas absorber is not less than $F_L^{min.water}$ and a water flow rate in an outlet liquid from the high pressure unreacted gas absorber is not less than $F_H^{min.water}$.

7. The method according to claim 5, wherein
the unreacted gas absorber includes a low pressure unreacted gas absorber to which water is fed as an absorbent, and a high pressure unreacted gas absorber to which an outlet liquid from the low pressure unreacted gas absorber is fed as an absorbent;
steps i to v are performed for each of the low pressure unreacted gas absorber and the high pressure unreacted gas absorber, so as to find:
$F_L^{min.water}$, which is $F^{min.water}$ for the low pressure unreacted gas absorber, and
$F_H^{min.water}$, which is $F^{min.water}$ for the high pressure unreacted gas absorber; and
in step vi, the flow rate of water fed to the low pressure unreacted gas absorber is controlled to a minimum value within a range in which a water flow rate in the outlet liquid from the low pressure unreacted gas absorber is not less than $F_L^{min.water}$ and a water flow rate in an outlet liquid from the high pressure unreacted gas absorber is not less than $F_H^{min.water}$.

* * * * *